(12) United States Patent
Schmid

(10) Patent No.: US 9,867,864 B2
(45) Date of Patent: Jan. 16, 2018

(54) USE OF SOMATOSTATIN ANALOGS IN CONTROL OF HYPOGLYCEMIA

(71) Applicant: Herbert Schmid, Neuenburg (DE)

(72) Inventor: Herbert Schmid, Neuenburg (DE)

(73) Assignee: Novartis AG, Basel (CH)

( * ) Notice: Subject to any disclaimer, the term of this patent is extended or adjusted under 35 U.S.C. 154(b) by 17 days.

(21) Appl. No.: 15/064,099

(22) Filed: Mar. 8, 2016

(65) Prior Publication Data

US 2016/0184388 A1    Jun. 30, 2016

Related U.S. Application Data

(63) Continuation of application No. 13/002,828, filed as application No. PCT/EP2009/058573 on Jul. 7, 2009, now Pat. No. 9,314,508.

(30) Foreign Application Priority Data

Jul. 8, 2008   (EP) ..................... 08159918

(51) Int. Cl.
| | |
|---|---|
| *A61K 38/00* | (2006.01) |
| *A61P 3/08* | (2006.01) |
| *A61P 3/10* | (2006.01) |
| *A61K 38/12* | (2006.01) |
| *A61K 38/31* | (2006.01) |

(52) U.S. Cl.
CPC .............. *A61K 38/12* (2013.01); *A61K 38/31* (2013.01)

(58) Field of Classification Search
CPC ....... A61K 38/00; A61K 38/12; C07K 14/655
See application file for complete search history.

(56) References Cited

U.S. PATENT DOCUMENTS

| 4,703,034 A | 10/1987 | Freidinger et al. | |
|---|---|---|---|
| 8,450,272 B2 * | 5/2013 | Schmid ................. | A61K 38/31 514/11.1 |
| 2003/0153494 A1 | 8/2003 | Gordon et al. | |

FOREIGN PATENT DOCUMENTS

| EP | 0063885 B1 | 11/1982 |
|---|---|---|
| WO | WO97/01579 A2 | 1/1997 |
| WO | WO02/10192 A2 | 2/2002 |
| WO | WO2005/046645 A1 | 5/2005 |
| WO | WO 2005053732 A1 | 6/2005 |
| WO | WO2007/096055 A1 | 8/2007 |

OTHER PUBLICATIONS

Van Der Hoek Joost et al., "The somatostatin analogue SOM230, compared with octreotide, induces differential effects in several metabolic pathways in acromegalic patients", Clinical Endocrinolgy, vol. 63, No. 2, pp. 176-184, 2005.
Eva Tiensuu Janson, "Treatment of neuroendocrine tumors with somatostatin analogs", Pituitary, vol. 9, No. 3, pp. 249-256, 2006.
"Diagnosis, classification and treatment of hypoglycemias", International Journal of Atherosclerosis, vol. 2, No. 2, pp. 120-123, 2007.
Usukura Mikiya et al., "Medical treatment of benign insulinoma using octreotide LAR: a case report", Endocrine Journal, vol. 54, No. 1, pp. 95-101, 2007.
Vezzosi D et al., "Short and long-term somatostatin analogue treatment in patients with hypoglycaemia related to endogenous hyperinsulinism", Clinical Endocrinology, vol. 68, No. 6, pp. 904-911, 2008.
Vezzosi Delphine et al., "Octreotide in insulinoma patients: efficacy on hypoglycemia, relationships with Octreoscan scintigraphy and immunostaining with anti-sst2A and anti-sstS antibodies", European Journal of Endocrinology, vol. 152, No. 5, pp. 757-767, 2005.
Gul Mehmet et al., "The effectiveness of various doses of octreotide for sulfonylurea-induced hypoglycemia after overdose", Advances in Therapy, vol. 23, No. 6, pp. 878-884, 2006.
Gonzalez Rita R et al., "Octreotide therapy for recurrent refractory hypoglycemia due to sulfonylurea in diabetes-related kidney failure", Endocrine Practice: Official Journal of the American College of Endocrinology and the American Association of Clinical Endocrinologists, vol. 13, No. 4, pp. 417-423, 2007.
Fasano Charles J et al., "Comparison of Octreotide and Standard Therapy Versus Standard Therapy Alone for the Treatment of Sulfonylurea-Induced Hypoglycemia", Annals of Emergency Medicine, vol. 51, No. 4, pp. 400-406, 2008.

* cited by examiner

*Primary Examiner* — Kaipeen Yang
(74) *Attorney, Agent, or Firm* — Michelle A. Han

(57) ABSTRACT

The present invention relates to the use of a Somatostatin (SRIF) analog which has a high binding affinity to human SSTR1,2,3,5, or a pharmaceutically acceptable salt thereof for the preparation of a pharmaceutical composition for the control of hypoglycemia.

1 Claim, 2 Drawing Sheets

USE OF SOMATOSTATIN ANALOGS IN CONTROL OF HYPOGLYCEMIA

The present invention relates to a new use of Somatostatin (SRIF) peptidomimetics (also referred to as Somatostatin- or SRIF-analogs).

BRIEF DESCRIPTIONS OF THE DRAWINGS

Figure 1:
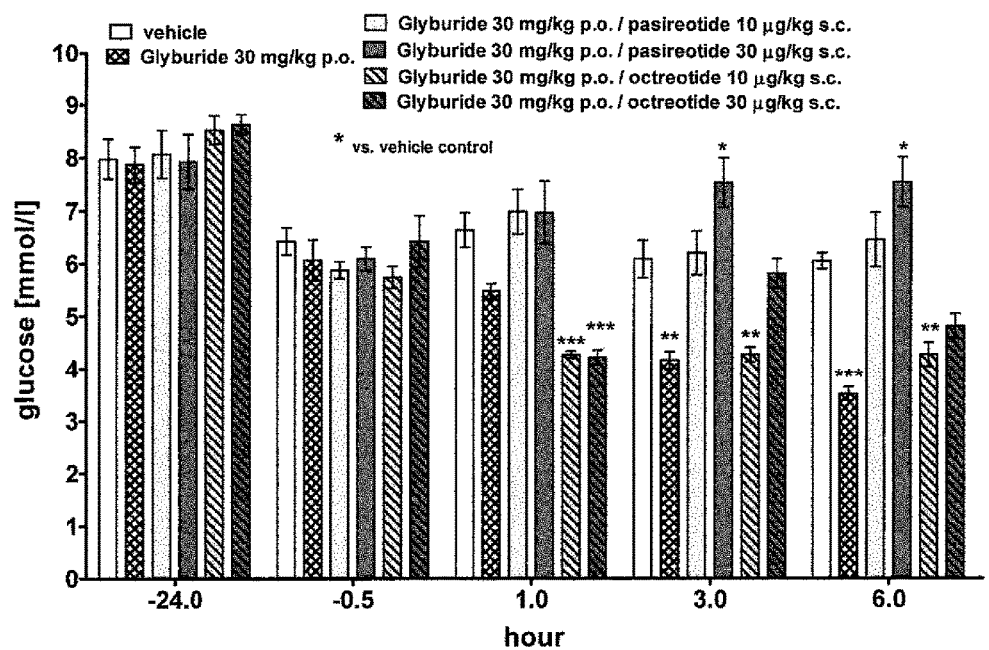

FIG. 1: Illustrates the effect of pasireotide, octreotide, and on glucose concentration in fasted rats FIG. 2: Illustrates the effect of pasireotide, octreotide, and glyburide on glucose concentration in fed rats Somatostatin is a tetradecapeptide having the structure

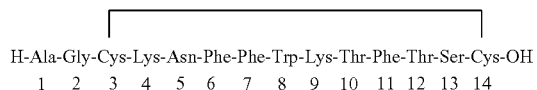

H-Ala-Gly-Cys-Lys-Asn-Phe-Phe-Trp-Lys-Thr-Phe-Thr-Ser-Cys-OH
 1   2   3   4   5   6   7   8   9  10  11  12  13  14

The somatostatin class is a known class of small peptides comprising the naturally occurring somatostatin-14 and analogues having somatostatin related activity, e.g. as disclosed by A. S. Dutta in Small Peptides, Vol. 19, Elsevier (1993). By "somatostatin analog" as used herein is meant any straight-chain or cyclic polypeptide having a structure based on that of the naturally occurring somatostatin-14 wherein one or more amino acid units have been omitted and/or replaced by one or more other amino radical(s) and/or wherein one or more functional groups have been replaced by one or more other functional groups and/or one or more groups have been replaced by one or several other isosteric groups. In general, the term covers all modified derivatives of the native somatostatin-14 which exhibit a somatostatin related activity, e.g. they bind to at least one of the five somatostatin receptor (SSTR), preferably in the nMolar range.

Natural somatostatin binds and activates all 5 somatostatin receptors (SSTR1-5) with nmol efficacy and thus causes its multiple physiological effects.

Synthetically available somatostatin analogs differ in their binding affinity to the different somatostatin receptor subtypes and often bind selectively to one or few subtypes with significantly higher affinity.

Somatostatin analogs of particular interest according to the present invention have a high binding affinity to human SSTR1,2,3,5 and have been described e.g. in WO 97/01579, the contents of which being incorporated herein by reference. Said somatostatin analogs comprise the amino acid sequence of formula I -(D/L)Trp-Lys-$X_1$-$X_2$- wherein $X_1$ is a radical of formula (a) or (b)

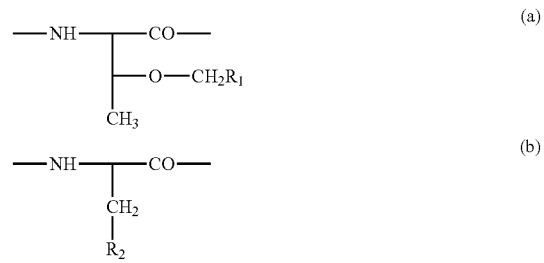

wherein $R_1$ is optionally substituted phenyl, wherein the substituent may be halogen, methyl, ethyl, methoxy or ethoxy,

wherein $Z_1$ is O or S, and
$X_2$ is an α-amino acid having an aromatic residue on the $C_\alpha$ side chain, or an amino acid unit selected from Dab, Dpr, Dpm, His,(Bzi)HyPro, thienyl-Ala, cyclohexyl-Ala and t-butyl-Ala, the residue Lys of said sequence corresponding to the residue Lys$^9$ of the native somatostatin-14.

Somatostatin analogs of particular interest which have a high binding affinity to human SSTR1,2,3,5 have also been described e.g. in WO02/10192, the contents of which being incorporated herein by reference. Said somatostatin analogs comprise the compound of formula

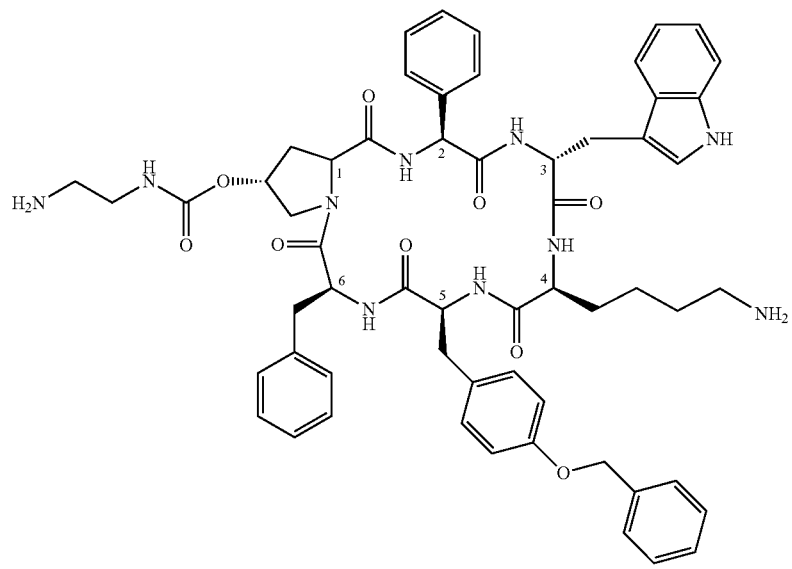 [SMILES: NCCCC[C@@H]1NC(=O)[C@@H](Cc2c[nH]c3ccccc23)NC(=O)[C@H](c2ccccc2)NC(=O)C2C[C@@H](OC(=O)NCCN)CN2C(=O)[C@H](Cc2ccccc2)NC(=O)[C@H](Cc2ccc(OCc3ccccc3)cc2)NC1=O]

also called cyclo[{4-(NH$_2$—C$_2$H$_4$—NH—CO—O—)Pro}-Phg-DTrp-Lys-Tyr(4-Bzl)-Phe] or pasireotide, as well as diastereoisomers and mixtures thereof, in free form, in salt or complex form or in protected form. Phg means —HN—CH(C$_6$H$_5$)—CO— and Bzl means benzyl.

Especially preferred according to the present invention is the use of pasireotide or a pharmaceutically acceptable salt thereof.

There are multiple etiologies and mechanisms for hypoglycemia. Hypoglycemia can be classified as hyperinsulinemic or hypoinsulinemic (Griffith MJ and Gamma R 2005 Hospital Medicine Vol 66(5)). The causes of hyperinsulinemic hypoglycemia can be due to multiple causes such as congenital disorders of hyperinsulinism, insulinomas, postprandial disorders (such as dumping syndrome and non-insulinoma pancreatogenous hypoglycemia) and the use of insulin secretagogues such as the sulfonylureas and meglitinides (Kappor RR et al, 2009.Nature Clinical Practice Endocrinology and Metabolism 5:101-112).

Hypoglycemia is a common presenting sign in emergency department patients. Sulfonylureas are a widely prescribed class of oral medications for the treatment of diabetes. Sulfonylureas are believed to stimulate insulin release from pancreatic beta-cells through a complex mechanism culminating in calcium influx and release of stored insulin from secretory granules within the pancreas. A frequent and well reported adverse reaction of sulfonylurea administration is persistent hypoglycemia, often necessitating hospital admission for serial glucose determinations. Other type diabetes type 2 drugs acting on pancreatic-beta cells such as e.g. meglitinides also suffer of hypoglycemia as adverse reaction.

Octreotide was reportedly used as an antidote in adverse reaction of sulfonylurea administrations (Lai MW, Klein-Schwartz W, Rodgers GC, et al. 2005 Annual report of the American Association of Poison Control Centers' national poisoning and exposure database. Clin Toxicol. 2006;44: 803-932).

A small randomized, double-blind trial suggested that octreotide can improve control of hypoglycemia (Fasana et al., Annals of Emergency Medicine, Vol 51(4), pate 400-406). In patients receiving octreotide, serum glucose level was higher than that in controls but waned within 8 hours. Normal glucose levels could not be established using octreotide. Thus, the authors conclude that, in order to change clinical practice to control hypoglycemia, multiple doses or continuous infusion is likely needed to prolong duration of effect by octreotide.

Given the limitations of octreotide for control of hypoglycemia, as well as the lack of alternative treatment options, there is a compelling need to develop new pharmacological approaches to control hypoglycemia.

Surprisingly, it has been found that the compounds according to the present invention, which have a high binding affinity to several SSTR, especially SSTR1,2,3,5, e.g. pasireotide, is much more effective in the treatment of hypoglycemia, in particular of endogenous hyperin-sulinemic hypoglycemia, than octreotide and can be used to establish normal glucose levels in hypoglycemic patients.

In one aspect, the present invention relates to the use of a Somatostatin (SRIF) analog which has a high binding affinity to human SSTR1,2,3,5, e.g. pasireotide, or a pharmaceutically acceptable salt thereof for the preparation of a pharmaceutical composition for the treatment or control of hypoglycemia, in particular of endogenous hyperinsulinemic hypoglycemia, such as congenital hyperinsulinemic hypoglycemia, dumping syndrome and drug-induced endogenous hyperinsulinemic hypoglycemia (e.g. sulfonylurea-induced hypoglycemia, meglitinide-induced hypoglycemia) or other compounds and condition which lead to an increase in insulin secretion, which is not accompanied or caused by an elevated plasma glucose level. In another aspect, the present invention relates to the use of a Somatostatin (SRIF) analog which has a high binding affinity to human SSTR1, 2,3,5, e.g. pasireotide, or a pharmaceutically acceptable salt thereof for the preparation of a pharmaceutical composition for the prevention of recurrent hypoglycemia, caused by increase in insulin secretion, which is not accompanied by an elevated plasma glucose level e.g. after sulfonylurea-induced exposure.

Sulfonurea antidiabetic drugs are well known in the art and include e.g. carbutamide, chlorpropamide, glibenclamide (glyburide), gliclazide, glimepiride, glipizide, gliquidone, tolazamide, tolbutamide.

In another embodiment, the present invention relates to the use of a Somatostatin (SRIF) analog which has a high binding affinity to human SSTR1,2,3,5, e.g. pasireotide, or a pharmaceutically acceptable salt thereof for the preparation of a pharmaceutical composition for the treatment of hypoglycemic conditions related to hyperinsulinemic conditions, such as Insulinoma and congenital hyperinsulinemic hypoglycemia which sporadically occurs in neotnates.

Further hypoglycemic conditions related to hyperinsulinemia which, in accordance with the present invention, are effectively treated by a Somatostatin (SRIF) analog which has a high binding affinity to human SSTR1,2,3,5, e.g. pasireotide are for instance described in E. Seaborg, Endocrine News May 2009, page 12 to 15 (e.g. table 1 and 2) which is herewith incorporated by reference, and include for instance:

1. Functional beta-cell disorders (Nesidioblastosis)
2. Paraneoplastic hyperinsulinism 3. Noninsulinoma pancreatogenous hypoglycemia syndrome (NIPHS)
4. Overdose of insulin secretagougues such as sulfonylureas, nateglinide or repaglinide
5. Insulinoma (hypoglycemia caused by insulinoma)
6. Congenital hypeinsulinemic hypoglycemia including patients with mutations to the following genes: ABCC8, KCNJ11, HASH, GGK, GLUD1, HNF4A and SLC16A1
7. Noninsulinoma pancreatogenous hypoglycemia syndrome (NIPHS)
8. Post-prandial reactive hypoglycemia (secondary to hyperinsulinism) including dumping syndrome
9. Hypoglycemia in the Beckwith-Wiedemann syndrome
10. Islet hyperplasia causing hypoglycemia
11. Hypoglycemia in patients with falciparum malaria.12. Insulin autoimmune hypoglycemia (antibody to insulin or antibody to insulin receptor)
12. Hypoglycemia caused by drugs, e.g.:
  i) alcohol ii) Cibezoline, Gatifloxin, Pentamidine, Quinine, Indomethacin, Glucagon (during endoscopy)
  iii) Chloroquineoxaline sulfonamide, Artesunate/artemisinlartemether, IGF-1, Litium, Propoxyphene/dextropropoxyphene
  iv) Angiotensin converting enzyme inhibitors, Angiotensin receptor antagonists, beta-Adrenergic receptor antagonists, Levofloxacin, Mifepristone, Disopyramide, Trimehtoprim-sulfamethoxazole, Heparin, 6-mercaptopurine
13. Critical illnesses such as hepatic, renal or cardiac failure, sepsis, inanition 14. Hormone deficiency, e.g. deficiency of cortisol ,or glucacon or epinephrine (in insulin-dependent diabetes mellitus.

It has been found in accordance with the present invention that Somatostatin (SRIF) analog which has a high binding affinity to human SSTR1,2,3,5, e.g. pasireotide can have an anti-proliferative effects Insulinomas. Thus, in another embodiment, the invention relates to the use of a Somatostatin (SRIF) analog which has a high binding affinity to human SSTR1,2,3,5, e.g. pasireotide, or a pharmaceutically acceptable salt thereof for the preparation of a pharmaceutical composition for the treatment of the proliferative effect of an insulinoma.

Hypoglycemia in accordance with the present application refers to a condition in which the blood sugar drops to an abnormally low level which can not easily controlled by an oral uptake of carbohydrates. Endogenous hyperinsulinemic hypoglycemia in accordance with the present application refers to a condition in which the blood sugar drops to an abnormally low level which can not easily controlled by an oral uptake of carbohydrates and there is evidence of increased endogenous secretion of insulin in spite of the low blood glucose levels. As understood in accordance with the present invention, the term "endogenous hyperinsulinemia" includes any hyperinsulinic condition which is not caused by exogenous insulin. In humans a blood glucose level below 70 mg/dl can be considered as abnormally low. In healthy individuals, symptoms of hypoglycemia develop at a mean plasma glucose concentration of approximately 55 mg/dl (3.0 mmol/liter) according to the Endocrine Society's Clinical Guidlines (Journal of Clinical Endocrinology & Metabolism, March 2009, 94(3): 709-728). The findings of symptoms, signs, or both with plasma concentrations of glucose less than 55 mg/dl (3.0 mmol/liter), insulin of at least 3.0 µU/ml (18 pmol/liter), C-peptide of at least 0.6 ng/ml (0.2 nmol/liter), and proinsulin of at least 5.0 pmol/liter document endogenous hyperinsulinism according to the Endocrine Society's Clinical Guidlines.

Control of hypoglycemia refers to the prevention or treatment of a condition of hypoglycemia such that the blood sugar level is increased toward normal blood sugar, or ideally normal blood sugar level is established. Normal blood sugar levels are known in the art, e.g. in humans a blood sugar level of 70-125 mg/dl.

The term "SRIF-analog with a high binding affinity to human SSTR1,2,3,5" as used herein (also referred to as COMPOUND OF THE INVENTION) refers to compounds which have a high binding affinity to SSTR1, SSTR2, SSTR3 and SSTR5, preferentially an 1050<10 nmol/l at SSTR1 and SSTR2 and an IC50<3 nmol/1 at SSTR3 and SSTR5; (Schmid et al., Neuroendocrinol. 2004;80:47-50). An especially preferred COMPOUND OF THE INVENTION is pasireotide or a pharmaceutically acceptable salt thereof.

The term insulin secretagogues as used herein refers to substances that that stimulate the beta cell to secrete insulin. Secretagogues include for instance the sulfonylureas and glinides, such as e.g. sulfonylureas, nateglinide or repaglinide.

It can be shown by established test models that the use of COMPOUND OF THE INVENTION results in an effective prevention and/or treatment of hypoglycemia, e.g. sulfonylurea-induced hypoglycemia and in particular treatment of endogenous hyperinsulinemic hypoglycemia.

In accordance with the particular findings of the invention, the present invention also provides a method of treating hypoglycemia and in particular treatment of endogenous hyperin-sulinemic hypoglycemia in a subject in need thereof comprising administering to said subject a therapeutically effective amount of a COMPOUND OF THE INVENTION or a pharmaceutically acceptable salt thereof.

The present invention relates also to a pharmaceutical composition for treatment of hypoglycemia, e.g. sulfonylurea-induced hypoglycemia, and in particular treatment of endogenous hyperinsulinemic hypoglycemia comprising a therapeutically effective amount of a COMPOUND OF THE INVENTION or a pharmaceutically acceptable salt thereof, together with one or more pharmaceutically acceptable diluents or carriers.

The present invention relates also to a commercial package comprising a COMPOUND OF THE INVENTION together with instructions for use thereof in the treatment of hypoglycemia, e.g. sulfonylurea-induced hypoglycemia and in particular treatment of endogenous hyperinsulinemic hypoglycemia.

Pharmaceutical compositions for the treatment of hypoglycemia, e.g. sulfonylurea-induced hypoglycemia, comprise an effective amount of the Somatostatin analog in free base form or in pharmaceutically acceptable salt form together with one or more pharmaceutically acceptable diluent or carrier. Such compositions may be formulated in conventional manner. Somatostatin analogs may also be administered in sustained release form, e.g. in the form of implants, microcapsules, microspheres or nanospheres comprising e.g. a biodegradable polymer or copolymer, in the form of a liposomal formulation, or in the form of an autoget, e.g. a solid or semi-solid composition capable of forming a gel after interaction with patient's body fluids.

The COMPOUNDS OF THE INVENTION can, for example, be formulated as disclosed in WO05/046645 (especially pasireotide).

COMPOUNDS OF THE INVENTION or a pharmaceutically acceptable salt thereof may be administered by any conventional route, for example parenterally e.g. in form of injectable solutions or suspensions (including e.g. the sustained release form as indicated above), orally using a conventional absorption enhancer if necessary, in a nasal or a suppository form or topically, e.g. in the form of an ophthalmic liquid, gel, ointment or suspension preparation, e.g. a liposomal, microsphere or nanosphere formulation, e.g. for instillation or subconjunctival or intra- or peri-ocular injections.

The present pharmaceutical compositions are prepared in a manner known per se, and comprise approximately from 1% to 100%, preferentially from approximately 1% to 40%, especially from approximately 20% to 30%, active ingredient.

The structure of the active ingredients identified by code nos., generic or trade names may be taken from the actual edition of the standard compendium "The Merck Index" or from databases, e.g. Patents International (e.g. IMS World Publications). The corresponding content thereof is hereby incorporated by reference. Any person skilled in the art is fully enabled to identify the active ingredients and, based on these references, likewise enabled to manufacture and test the pharmaceutical indications and properties in standard test models, both in vitro and in vivo.

It will be understood that in the discussion of methods, references to the active ingredients are meant to also include the pharmaceutically acceptable salts. If these active ingredients have, for example, at least one basic center, they can form acid addition salts. Corresponding acid addition salts can also be formed having, if desired, an additionally present basic center. The active ingredients having an acid group (for example COOH) can also form salts with bases. Salts include acid addition salts with e.g. inorganic acids, polymeric acids or organic acids, for example with hydrochloric acid, acetic acid, lactic acid, aspartic acid, benzoic acid, succinic acid or pamoic acid. Acid addition salts may exist as mono- or divalent salts, e.g. depending whether 1 or 2 acid equivalents are added to the COMPOUND OF THE INVENTION in free base form. Preferred salts are tha lactate, aspartate, benzoate, succinate and pamoate including mono- and disalts, more preferably the aspartate di-salt and the pamoate monosalt, e.g. of pasireotide.

The active ingredient or a pharmaceutically acceptable salt thereof may also be used in form of a hydrate or include other solvents used for crystallization.

The person skilled in the pertinent art is fully enabled to select a relevant test model to prove the hereinbefore and hereinafter indicated therapeutic indications and beneficial effects.

The pharmacological activity of a COMPOUND OF THE INVENTION in hypoglycemia, e.g. sulfonylurea-induced hypoglycemia, and in particular treatment of hyperinsulinemic hypoglycemia may, for example, also be demonstrated in clinical studies. Such clinical studies are preferably randomized, double-blind, clinical studies in patients suffering from hypoglycemia, e.g. sulfonylurea-induced hypoglycemia and in particular treatment of hyperinsulinemic hypoglycemia.

The effective dosage of the active ingredients employed may vary depending on the particular compound or pharmaceutical composition employed, the mode of administration, the severity of the condition being treated. Thus, the dosage regimen is selected in accordance with a variety of factors including the route of administration and the renal and hepatic function of the patient. A physician, clinician or veterinarian of ordinary skill can readily determine and prescribe the effective amount of the single active ingredients required to prevent, ameliorate or arrest the progress of the condition. Optimal precision in achieving concentration of the active ingredients within the range that yields efficacy without toxicity requires a regimen based on the kinetics of the active ingredients' availability to target sites. This involves a consideration of the distribution, equilibrium, and elimination of the active ingredients. For instance, pasireotide may be administered as a monthly depot with a dose of 20 mg, 40 mg, 60 mg, 80 mg or 100 mg, or as intramuscular or intravenous injections 100, 200, 300, 400 or 500 mcg two to four times a day (e.g. bid, tid).

EXAMPLES

Figure 2:
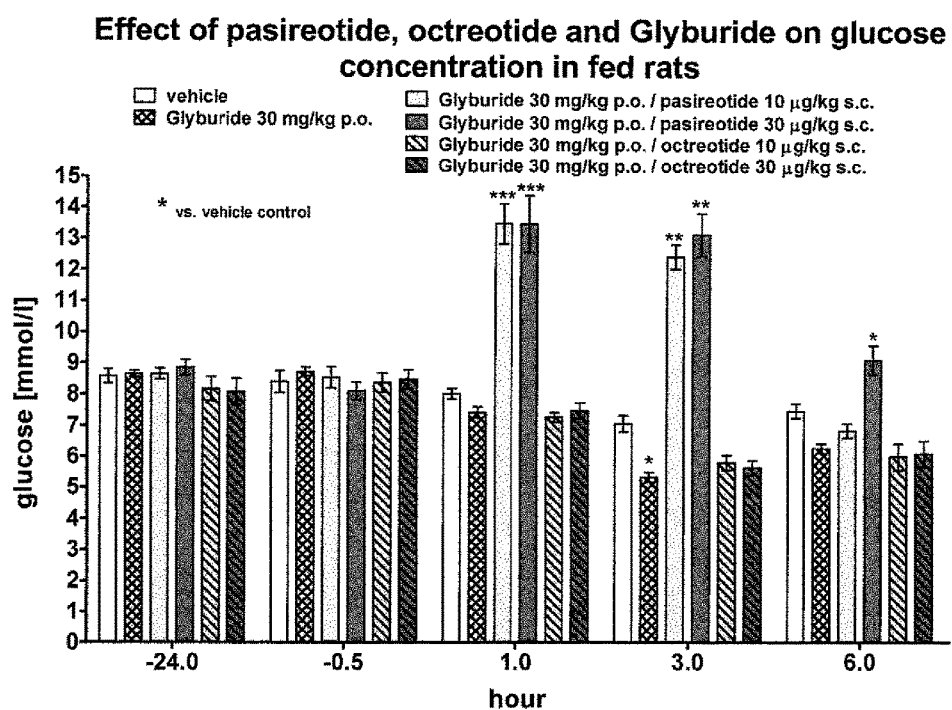

In order to investigate the effect of octreotide and pasireotide on glyburide induced hypoglycemia adult male Lewis rats were fasted for 24 h and then received an oral dose of Glyburide (30 mg/kg) immediately followed by a s.c. injection of either pasireotide (10 or 30 µg/kg) or octreotide (10 or 30 µg/kg). Food restricton for 24 h reduced plasma glucose concentration in all treatment groups from about 8 mmol/l to approximately 6 mmol/l. 30 min abefore the application of the compound (FIG. 1, Table 1). Glyburide alone reduced plasma glucose levels significantly 1, 3 and 6 h after the application (minimum 3.5 mmol/l 6 h after the application of glyburide). 1, 3 and 6 h after the application of pasireotide in glyburide treated rats, plasma glucose increased to levels of untreated fasted rats or above. The effect was dose dependent suggesting that by adding an appropriate dose of pasireotide it is possible to overcome or even exceed the hypoglycemic effect of glyburide. Octreotide was not effective to prevent the glyburide induced hypoglycemia after 1 h and showed only a small tendency to increase glucose levels in glyburide treated rats at the highest dose after 3 and 6 h. In fed rats the hypoglycemic effect of glyburide was not very pronounced and pasireotide, in-contrast to octreotide) caused a significant but transit effect on plasma glucose (FIG. 2, Table 2). These experiments suggest that in fed as well as fasted rats pasireotide is able to increase plasma glucose in rats pretreated with an hypoglycemic agent (e.g. glyburide).

TABLE 1

| compound | glucose −24 h [mmol/L] | glucose −30 min [mmol/L] | glucose 1 h [mmol/L] | glucose 3 h [mmol/L] | glucose 6 h [mmol/L] |
| --- | --- | --- | --- | --- | --- |
| vehicle 2 ml/kg p.o. 1 ml/kg s.c. fasted animals | 7.98 ± 0.37 | 6.43 ± 0.26 | 6.65 ± 0.33 | 6.10 ± 0.36 | 6.07 ± 0.15 |
| Glyburide 30 mg/kg p.o. fasted animals | 7.87 ± 0.34 | 6.07 ± 0.39 | 5.48 ± 0.15 | 4.17 ± 0.16 * | 3.53 ± 0.13 |
| Glyburide 30 mg/kg p.o. + pasireotide 10 µg/kg s.c. fasted animals | 8.07 ± 0.45 | 5.88 ± 0.16 | 7.00 ± 0.42 *** | 6.22 ± 0.42 ** | 6.48 ± 0.52 |
| Glyburide 30 mg/kg p.o. + pasireotide 30 µg/kg s.c. fasted animals | 7.93 ± 0.52 | 6.10 ± 0.23 | 6.98 ± 0.59 *** | 7.55 ± 0.47 ** | 7.58 ± 0.47 * |
| Glyburide 30 mg/kg p.o. + octreotide 10 µg/kg s.c. fasted animals | 8.53 ± 0.27 | 5.75 ± 0.21 | 4.27 ± 0.07 | 4.28 ± 0.14 | 4.28 ± 0.23 |
| Glyburide 30 mg/kg p.o. + octreotide 30 µg/kg s.c. fasted animals | 8.63 ± 0.19 | 6.43 ± 0.49 | 4.22 ± 0.14 | 5.83 ± 0.28 | 4.83 ± 0.24 |

* vs. vehicle control
One-way ANOVA Dunnet test

TABLE 2

| compound | glucose −24 h [mmol/L] | glucose −30 min [mmol/L] | glucose 1 h [mmol/L] | glucose 3 h [mmol/L] | glucose 6 h [mmol/L] |
| --- | --- | --- | --- | --- | --- |
| vehicle 2 ml/kg p.o. 1 ml/kg s.c. fed animals | 8.58 ± 0.23 | 8.40 ± 0.36 | 8.02 ± 0.17 | 7.07 ± 0.26 | 7.48 ± 0.23 |

TABLE 2-continued

| compound | glucose −24 h [mmol/L] | glucose −30 min [mmol/L] | glucose 1 h [mmol/L] | glucose 3 h [mmol/L] | glucose 6 h [mmol/L] |
|---|---|---|---|---|---|
| Glyburide 30 mg/kg p.o. fed animals | 8.65 ± 0.11 | 8.72 ± 0.14 | 7.42 ± 0.18 | 5.33 ± 0.16 ** | 6.27 ± 0.16 *** |
| Glyburide 30 mg/kg p.o. + pasireotide 10 µg/kg s.c. fed animals | 8.65 ± 0.18 | 8.53 ± 0.34 | 13.48 ± 0.65 | 12.42 ± 0.39 | 6.85 ± 0.23 |
| Glyburide 30 mg/kg p.o. + pasireotide 30 µg/kg s.c. fed animals | 8.85 ± 0.25 | 8.10 ± 0.29 | 13.47 ± 0.91 | 13.13 ± 0.69 * | 9.12 ± 0.47 * |
| Glyburide 30 mg/kg p.o. + octreotide 10 µg/kg s.c. fed animals | 8.17 ± 0.38 | 8.37 ± 0.31 | 7.27 ± 0.15 *** | 5.80 ± 0.24 ** | 6.00 ± 0.44 ** |
| Glyburide 30 mg/kg p.o. + octreotide 30 µg/kg s.c. fed animals | 8.07 + 0.43 | 8.47 ± 0.31 | 7.48 ± 0.25 *** | 5.63 ± 0.24 | 6.10 ± 0.43 |

* vs. vehicle control
One-way ANOVA Dunnet test

What is claimed:

1. A method of treating post-prandial reactive hypoglycemia consisting of administering to a patient in need thereof pasireotide or a pharmaceutically acceptable salt thereof.

* * * * *